US009393537B2

(12) United States Patent
Hamers et al.

(10) Patent No.: US 9,393,537 B2
(45) Date of Patent: Jul. 19, 2016

(54) JET LOOP REACTOR HAVING NANOFILTRATION

(71) Applicants: Bart Hamers, VG Horst (NL); Dirk Fridag, Haltern am See (DE); Robert Franke, Marl (DE); Marc Becker, Dortmund (DE); Markus Priske, Mobile, AL (US)

(72) Inventors: Bart Hamers, VG Horst (NL); Dirk Fridag, Haltern am See (DE); Robert Franke, Marl (DE); Marc Becker, Dortmund (DE); Markus Priske, Mobile, AL (US)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/810,807

(22) Filed: Jul. 28, 2015

(65) Prior Publication Data

US 2015/0336078 A1 Nov. 26, 2015

Related U.S. Application Data

(63) Continuation of application No. 14/343,917, filed as application No. PCT/EP2012/067513 on Sep. 7, 2012, now Pat. No. 9,149,780.

(30) Foreign Application Priority Data

Sep. 9, 2011 (DE) .......................... 10 2011 082 441

(51) Int. Cl.
C07C 45/50 (2006.01)
B01J 19/00 (2006.01)
B01J 8/00 (2006.01)
B01J 19/24 (2006.01)
B01J 4/00 (2006.01)

(52) U.S. Cl.
CPC ................ *B01J 8/0065* (2013.01); *B01J 4/002* (2013.01); *B01J 19/2435* (2013.01); *B01J 19/2445* (2013.01); *B01J 19/2475* (2013.01); *C07C 45/50* (2013.01); *C07C 45/505* (2013.01); *B01J 2219/24* (2013.01)

(58) Field of Classification Search
CPC . C07C 45/505; B01J 19/2435; B01J 19/2445; B01J 19/2475
USPC .......................................... 568/451; 422/187
See application file for complete search history.

(56) References Cited

U.S. PATENT DOCUMENTS

| 6,350,911 | B1 | 2/2002 | Sander et al. |
| 6,482,992 | B2 | 11/2002 | Scholz et al. |
| 7,064,237 | B2 | 6/2006 | Zehner et al. |
| 7,091,383 | B2 | 8/2006 | Vanoppen et al. |
| 8,226,829 | B2 | 7/2012 | Wiese et al. |
| 8,389,774 | B2 | 3/2013 | Becker et al. |
| 2006/0014970 | A1 | 1/2006 | Goebbel et al. |
| 2008/0251456 | A1 | 10/2008 | Wiese et al. |
| 2011/0144391 | A1 | 6/2011 | Becker et al. |
| 2012/0035382 | A1 | 2/2012 | Priske et al. |
| 2012/0046503 | A1 | 2/2012 | Priske et al. |

FOREIGN PATENT DOCUMENTS

| DE | 198 57 409 | 6/2000 |
| JP | 2002-53501 A | 2/2002 |
| JP | 2002-532454 A | 10/2002 |
| JP | 2009-513320 A | 4/2009 |
| WO | 2004 037803 | 5/2004 |
| WO | 2010 023018 | 3/2010 |

OTHER PUBLICATIONS

Office Action issued Jun. 22, 2015 in Japanese Patent Application No. 2014-528992 (submitting English translation only).
International Search Report Issued Nov. 14, 2012 in PCT/EP12/067513 Filed Sep. 7, 2012.
Search Report and Written Opinion issued Jun. 2, 2015, in Singapore Patent Application No. 11201400458Q.
Koen de Smet et al., Nanofiltration-coupled catalysis to combine the advantages of homogeneous and heterogeneous catalysis, Mar. 8, 2001.
David J. Cole-Hamilton, Homogeneous Catalysis—New approaches to catalyst separation, recovery and recycling, Mar. 14, 2003.

*Primary Examiner* — Sikarl Witherspoon
(74) *Attorney, Agent, or Firm* — Oblon, McClelland, Maier & Neustadt, L.L.P.

(57) ABSTRACT

The invention relates to a device for the continuous, homogeneous-catalysis reaction of a liquid with a gas and optionally an additional fluid, wherein the device comprises at least one reactor having an external liquid circulation driven by a pump, and wherein the device has at least one membrane separation stage that preferably holds back the homogeneous catalyst. The aim of the invention is to specify a device that allows homogeneous-catalysis gas/liquid phase reactions, in particular hydroformylations, which operate with membrane separation of the catalyst to be performed economically at an industrially relevant scale. Said aim is achieved in that a jet loop reactor is provided as the reactor, and that the pump and the membrane separation stage are arranged in the same external liquid circuit.

14 Claims, 9 Drawing Sheets

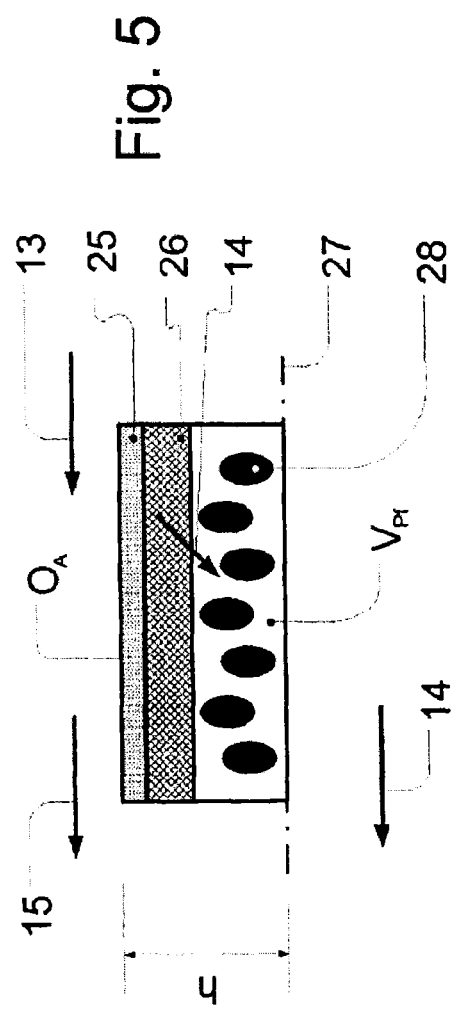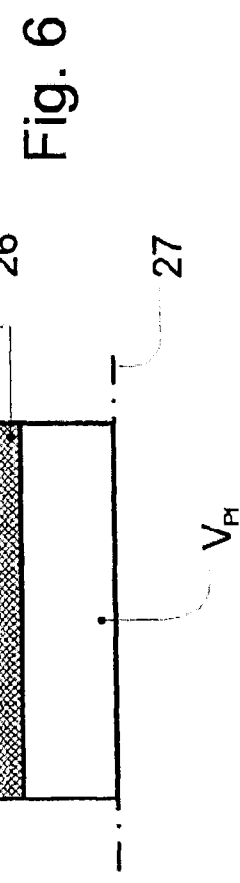

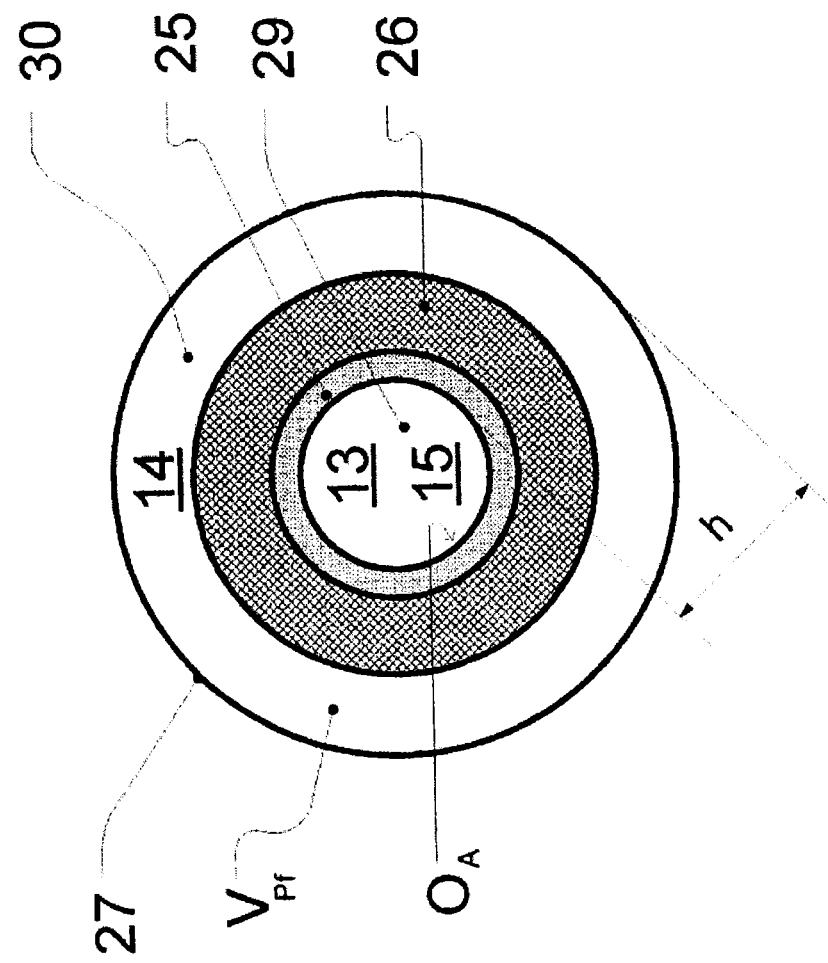

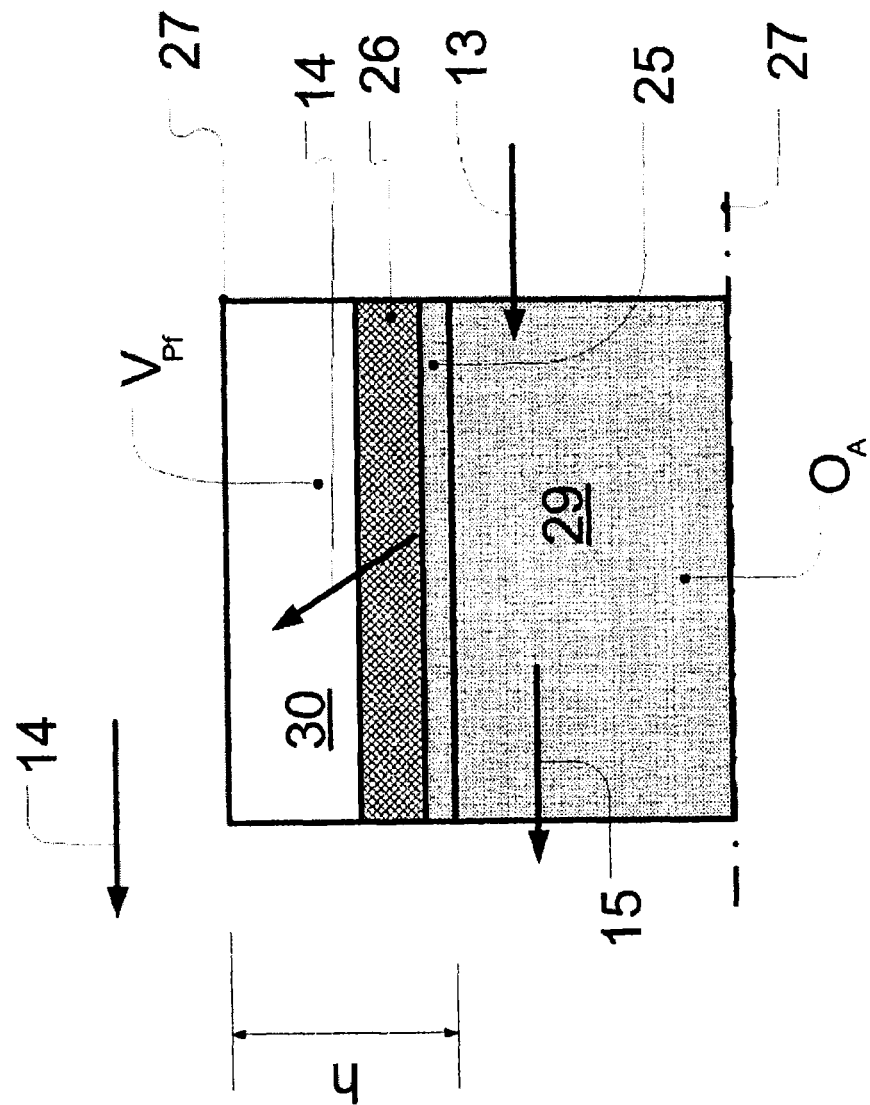

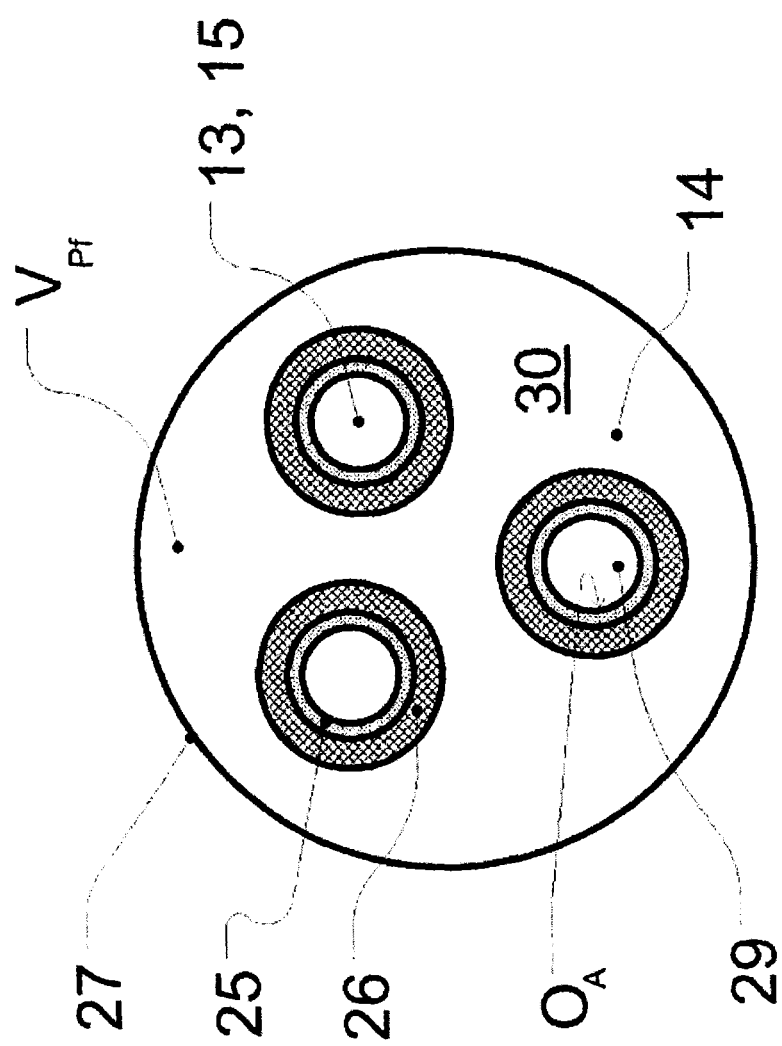

JET LOOP REACTOR HAVING NANOFILTRATION

CROSS-REFERENCE TO RELATED APPLICATIONS

Figure 1:
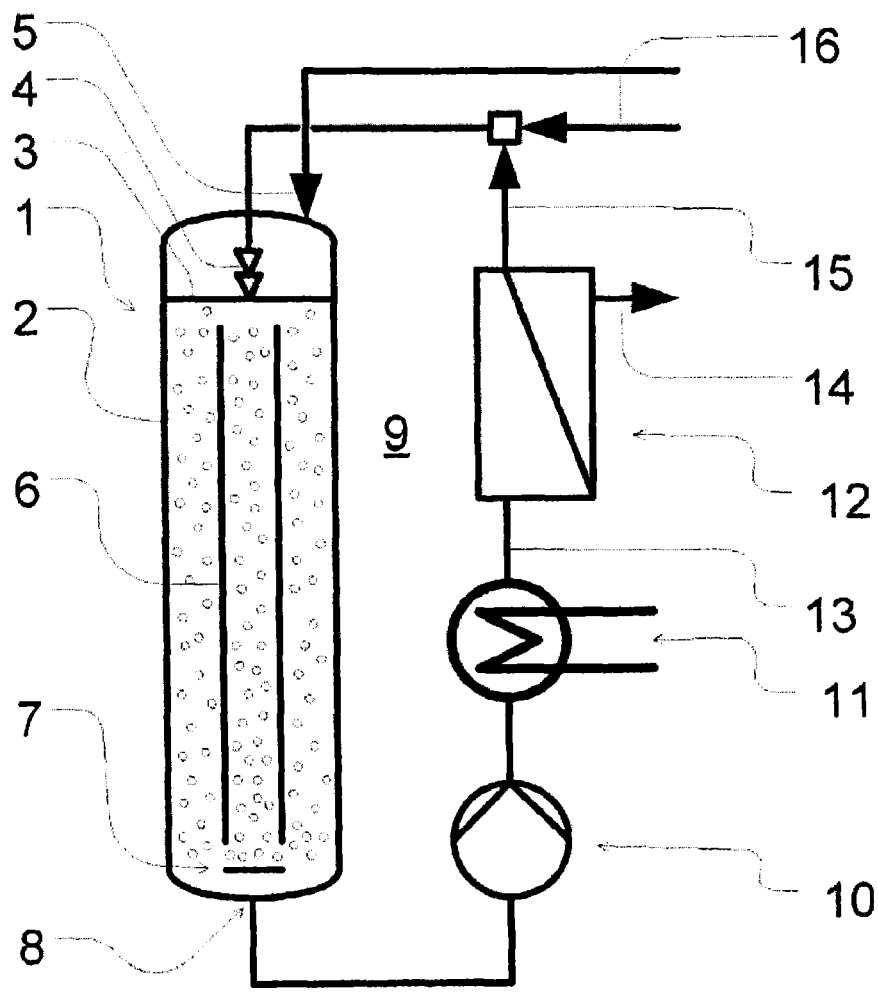

This application is a continuation of U.S. Ser. No. 14/343,917, filed Aug. 6, 2014, allowed, which is a U.S. national stage application of International Application No. PCT/EP12/067513, filed Sep. 7, 2012, which claims the benefit of priority from DE 10 2011 082 441.3, filed Sep. 9, 2011, the entire contents of which are incorporated herein by reference.

The invention relates to a device for the continuous homogeneous-catalytic reaction of a liquid with a gas and optionally a further fluid, wherein the device comprises at least one reactor having a pump-driven external liquid circuit, and wherein the device comprises at least one membrane separation stage that preferably retains the homogeneous catalyst.

A device of this type is known from Janssen, M., Wilting, J., Müller, C. and Vogt, D. (2010), Continuous Rhodium-Catalyzed Hydroformylation of 1-Octene with Polyhedral Oligomeric Silsesquioxanes (POSS) Enlarged Triphenylphosphine. Angewandte Chemie International Edition, 49: 7738-7741; doi: 10.1002/anie.201001926.

A liquid is a substantially incompressible free-flowing medium. A gas is a compressible free-flowing medium. A fluid is a liquid or a gas. A two-phase mixture of a homogeneously distributed liquid phase and a gas phase distributed dispersely therein is likewise a fluid within the meaning of this invention. On account of the gas fraction, fluids of this type are compressible to a slight extent.

In the context of the present invention, a supplied liquid is a substance or mixture of substances which is present in the apparatus under reaction conditions in the liquid state of matter and comprises at least one reactant. Gas is taken to mean a pure gas or a gas mixture which comprises at least one reactant and optionally an inert gas. An example of a gas which comprises two reactants is the synthesis gas that is used, for example, in hydroformylations and consists of hydrogen and carbon monoxide.

A jet loop reactor in the context of the invention is a device for the continuous reaction of a liquid and at least one further fluid, in which the liquid enters under pressure through a nozzle into a reaction space, flows through this along a main direction of flow, is reversed at the reaction space end situated opposite the nozzle, flows back in the opposite direction to the main direction of flow and is again accelerated in the main direction of flow, and so within the reactor space an internal liquid circuit (loop) is established. The second fluid is entrained by the liquid stream and reacts on the path along the loop. The liquid thus serves as motive jet medium.

For introduction of kinetic energy into the liquid, an external liquid circuit is assigned to the reaction space, in which external liquid circuit some of the liquid is circulated outside the reaction space. A pump which provides the kinetic energy to the liquid stream which is necessary for establishing the loop flow within the reactor is provided within the external liquid circuit. The nozzle is fed correspondingly from the external circuit.

A good introduction into the technique of jet loop reactors is offered in: P. Zehner, M. Krause: "Bubble Columns", Ullmann's Encyclopedia of Industrial Chemistry, Electronic Release, 7th ed., Chapter 4, Wiley-VCH, Weinheim [2005].

In hydroformylation (also termed oxo reaction), hydrocarbons having olefinic double bonds (alkenes) are reacted with synthesis gas (gas mixture of hydrogen and carbon monoxide) to form aldehydes and/or alcohols.

Fundamental introductions into hydroformylation are offered in Falbe, Jurgen: New Syntheses with Carbon Monoxide. Springer Verlag 1980, Berlin, Heidelberg, New York and Pruett, Roy L.: Hydroformylation. Advances in Organometallic Chemistry Vol. 17, Pages 1-60, 1979.

Hydroformylation serves for producing higher aldehydes. Higher aldehydes, in particular those having 3 to 25 carbon atoms, are used, for example, as synthesis precursors, for producing carboxylic acids, and as aroma substances. Technically they are frequently converted by catalytic hydrogenation to the corresponding alcohols which in turn serve for producing plasticizers and detergents. Owing to the commercial importance of hydroformylation products, the oxo reaction is carried out on an industrial scale.

In commercial hydroformylation, now, organophosphorus metal complex catalysts based on cobalt or rhodium are used. The catalysts are dissolved homogeneously in the liquid hydroformylation mixture. In the context of separation of the target product (the aldehydes) from the hydroformylation mixture, the homogeneous catalyst must also be separated off gently from the hydroformylation mixture, since the complex catalyst reacts in a comparatively sensitive manner to changes in state, and could lose its activity.

Traditionally, the catalyst is separated off from the hydroformylation mixture by distillation. In order to decrease the risk of deactivation and to lower energy consumption of the process, recently there have been efforts to separate off the homogeneously dissolved catalyst from the hydroformylation mixture using membrane technology (nanofiltration).

The fundamentals of membrane-supported organophilic nanofiltration for separating off homogeneously dissolved catalyst complexes from hydroformylation mixtures are described by Priske, M. et al.: Reaction integrated separation of homogeneous catalysts in the hydroformylation of higher olefins by means of organophilic nanofiltration. Journal of Membrane Science, Volume 360, Issues 1-2, 15 September 2010, Pages 77-83; doi:10.1016/j.memsci.2010.05.002.

In the membrane filtration of reactor discharges from hydroformylations, dissolved or non-dissolved synthesis gas frequently in the liquid reactor discharge is a peculiarity: Hydroformylation is a two-phase reaction, hydrogen and carbon monoxide form the gas phase, the alkenes, aldehydes and alcohols form the liquid phase in which the catalyst is dissolved so as to be solids-free. Part of the synthesis gas is also dissolved in the liquid reactor phase in accordance with the dissolution equilibrium in the reactor and is taken off together with the reactor discharge. As long as the synthesis gas remains dissolved in the reactor discharge during membrane filtration, the membrane filtration is to this extent problem-free. If, however, the liquid reactor discharge is accompanied by a gas phase, or if a gas phase is formed as bubbles during expansion at the membrane, the gas bubbles may be able to damage the membrane mechanically. Polymer membranes are particularly susceptible to damage by gas bubbles.

A further problem due to outgassing synthesis gas is the loss of carbon monoxide: In particular in the Rh-catalyzed hydroformylation, the CO partial pressure exercises a critical effect on the activity and stability of the catalyst complex. In order to avoid the loss of activity during the membrane separation of homogeneously dissolved complex catalysts from the reaction discharge of a hydroformylation, EP1931472B1 proposes ensuring a minimum partial CO pressure at all three connections of the membrane separation stage (feed, retentate, permeate).

WO2010023018A1 shows two jet loop reactors connected in parallel to one another having a shared external liquid circuit. The jet loop reactors are used with homogeneously dissolved catalysts in the hydroformylation. Separating off the catalyst is not thematized.

Janssen, M., Wilting, J., Müller, C. and Vogt, D. (2010), Continuous Rhodium-Catalyzed Hydroformylation of 1-Octene with Polyhedral Oligomeric Silsesquioxanes (POSS) Enlarged Triphenylphosphine. Angewandte Chemie International Edition, 49: 7738-7741. doi: 10.1002/anie.201001926 describe carrying out a homogeneously catalyzed hydroformylation in a special spray mist reactor which has two external liquid circuits contacted to one another in a crossflow chamber. In a first circuit, the liquid reactor discharge with synthesis gas dissolved therein is taken off from the reactor and circulated by means of a rotary vane pump. In a crossflow chamber, the reactor discharge is divided into two substreams: A first substream containing the liquid reactor discharge with dissolved synthesis gas as synthesis gas in gas phase is conducted along the first circuit back into the reactor. A second, purely liquid substream is transported by means of a pump through a ceramic membrane separation stage. There, the target product is taken off as permeate, the catalyst-containing retentate is passed via the second circuit strand back to the crossflow chamber and there mixed with the first liquid circuit. The advantage of this device is considered to be that the reactor discharge is degassed within the crossflow chamber and therefore any separating gas phases remain in the first circuit. This is because the particular flow conditions of the crossflow chamber favor a takeoff of the gas bubbles into the return of the first circuit. The second liquid circuit in which the membrane is arranged thus remains gas-free (this means $H_2$ and CO remain dissolved in the liquid). However, the disadvantage of this laboratory apparatus is the comparatively complicated structure thereof, the requirement for two pumps and the high flow-dynamic energy loss in the crossflow chamber: Hydroformylations on an industrial scale can scarcely be carried out economically in this device.

In view of this prior art, the object of the present invention is to specify a device which permits homogeneous-catalytic gas/liquid phase reactions, in particular hydroformylations, which operate with membrane separation of the catalyst, to be carried out on an industrially-relevant scale economically.

This object is achieved by a device according to claim 1.

The invention therefore relates to a device for the continuous homogeneous-catalytic reaction of a liquid with a gas and optionally a further fluid, which device comprises at least one jet loop reactor having a pump-driven external liquid circuit and which comprises at least one membrane separation stage that preferably retains the homogeneous catalyst, and in which pump and membrane separation stage are arranged in the same external liquid circuit.

The invention is based on the knowledge that a jet loop reactor and nanofiltration may be combined to form a device which permits economic carrying out of a hydroformylation on a commercial format. Fundamental to the economic efficiency of the process is simple structure of the process with as few plant components as possible and also marked retention and recirculation of the active catalyst to the reaction. A process reduced to the essential components results from the direct integration of the membrane separation into the external circuit of the jet loop reactor. This additionally permits separation of the catalyst and optionally of the free ligand under reaction conditions.

Use of commercially available membrane modules for reaction mixtures having dissolved and/or non-dissolved gas fractions is not possible, since they are not designed for adequate permeate-side gas removal and, depending on the amount of the permeate-side gas volumetric flow rate to be removed, build up a counterpressure on the permeate side which decreases the liquid permeate output or can even lead to destruction of the membrane. It has been found that using membrane modules which, per square meter of active membrane area, a permeate-side free volume of greater than 0.3 cubic decimeter ($dm^3$, equivalent to 1 liter) are necessary for gas streams occurring on the permeate side. The greater the permeate-side gas stream, the greater must the free permeate-side volume be. Surprisingly, it has additionally been found that the retention of the catalyst, in process streams containing a gas phase at the latest on the permeate side, is increased with the increase in permeate-side free volume.

A particularly preferred development of the invention therefore provides that a permeate-side free volume is provided in the membrane separation stage, which free volume is at least 0.3 $dm^3$ per $m^2$ of membrane surface.

Permeate-side volume is taken to mean the volume following on the permeate side perpendicular to the active membrane surface. The permeate-side free volume is the fraction of the permeate-side volume which is not filled with material apart from the permeate.

In a preferred embodiment of the invention, the pump is equipped structurally for long-term pumping of fluids which contain liquid and gaseous phases. Particularly preferably, pumps should be used which in addition can also transport a small solids fraction.

For this purpose, peripheral impeller pumps are particularly suitable. They can transport in the long term fluid mixtures which contain a liquid phase and a gaseous phase. Small solids fractions are not a problem. A peripheral impeller pump is a particular type of a centrifugal pump having an annular peripheral channel in which the pump rotor rotates. The pump rotor is usually constructed as a circular disk having a multiplicity of radially extending projections on the disk. The projections run in the region of the peripheral channel. The fluid is drawn in by suction through a suction port and passed through the annular channel in which the pump rotor rotates. This consists of straight paddles which place the fluid into a rotary motion. In the peripheral channel, therefore, the energy of motion is transferred from the paddles to the medium, as a result of which the pressure is increased. The fluid leaves the peripheral impeller pump through an outlet port after it has flowed through the peripheral channel. Peripheral impeller pumps are commercially available from K-ENGINEERING Mischtechnik and Maschinenbau, 26871 Papenburg (Germany) or from SPECK PUMPEN Verkaufsgesellschaft GmbH, 91231 Neunkirchen a. Sand (Germany).

In order to avoid deactivation of the catalyst and damage of the membrane due to degassing, and also to achieve an improved membrane retention, the permeate of the membrane separation stage needs to be degassed in a controlled manner. In addition to the permeate-side free volume dimensioned as above, a permeate-side gas discharge needs to be provided arranged downstream of the membrane separation stage. Such a gas discharge should be constructed as follows:

The core piece of the gas discharge is a compensating vessel in which liquid and gaseous phases are separated from one another. The two-phase permeate stream is fed to the vessel in order that liquid phase and gas phase can separate. A pressure maintaining device which removes gas until the preset pressure is reached is connected to the gas phase. In addition, a compressed gas feed is mounted on the vessel, which compressed gas feed permits the preset gas pressure to be held constant, for instance when the liquid level in the vessel is falling.

The suitable membrane material must be selected with respect to the catalyst complex that is to be separated off:

Since the permeability of a membrane for the various components of the feed that is to be separated is ultimately a function of time (the membrane is not absolutely impermeable to a catalyst, its passage velocity is rather markedly slower in relation to the other reaction participants), the membrane must be selected in such a manner that the catalyst complex that is to be separated off is retained preferentially.

In the process according to the invention membranes can be used which, owing to their chemical or physical properties, are suitable for retaining organophosphorus metal-complex catalyst and/or free organophosphorus ligand preferably to an extent of at least 50%.

Corresponding membranes belong to the class of nanofiltration membranes. The expression nanofiltration is applied to membrane separation processes which have a separation limit or molecular weight cutoff (MWCO) in the range from 150 g/mol to over 1 nm. The magnitude of the separation limit or MWCO indicates the molecular or particle size of a component that has a membrane retention of 90%.

A usual method of determination for the separation limit is given in Y. H. See Toh, X. X. Loh, K. Li, A. Bismarck, A. G. Livingston, In search of a standard method for the characterisation of organic solvent nanofiltration membranes, J. Membr. Sci., 291 (2007) 120-125.

The membrane retention $R_i$ is calculated from the feed-side concentration of the component i under consideration at the membrane $x_{iF}$ and the permeate-side concentration of component i under consideration at the membrane $x_{iP}$ as follows:

$$R_i = 1 - x_{iP}/x_{iF}$$

Preferably, the membranes for the use according to the invention should have an MWCO of less than 1000 g/mol.

A further precondition for the usability of the membrane is that the membrane must be stable to all compounds present in the reaction mixture, in particular to the solvents. Membranes are also considered to be stable which experience a change with time of the MWCO and/or of the permeability—for instance caused by swelling of the membrane polymer, but fulfill the separation task over the service life. Furthermore, the membrane material should withstand the reaction temperature. Membrane materials which are stable and perform well at the reaction temperature permit complex temperature control to be dispensed with.

Preferably, membranes are used which have an active separation layer made of a material selected from cellulose acetate, cellulose triacetate, cellulose nitrate, regenerated cellulose, polyimides, polyamides, polyether ether ketones, sulfonated polyether ether ketones, aromatic polyamides, polyamide-imides, polybenzimidazoles, polybenzimidazolones, polyacrylonitrile, polyarylether sulfones, polyesters, polycarbonates, polytetrafluoroethylene, polyvinylidene fluoride, polypropylene, polydimethylsiloxane, silicones, polyphosphazenes, polyphenyl sulfides, polybenzimidazoles, 6.6 Nylon, polysulfones, polyanilines, polyurethanes, acrylonitrile/glycidyl methacrylate (PANGMA), polytrimethylsilylpropynes, polymethylpentynes, polyvinyltrimethylsilane, alpha-aluminum oxides, titanium oxides, gamma-aluminum oxides, polyphenylene oxide, silicon oxides, zirconium oxides, silane-hydrophobized ceramic membranes, as are described in DE10308111, polymers having intrinsic microporosity (PIM) such as PIM-1 and others, as are described, e.g., in EP0781166 and in "Membranes" by I. Cabasso, Encyclopedia of Polymer Science and Technology, John Wiley and Sons, New York, 1987. The abovementioned substances can be present in crosslinked form in particular in the active separation layer, optionally by addition of auxiliaries, or as what are termed mixed matrix membranes provided with fillers such as, e.g., carbon nanotubes, metal organic frameworks or hollow spheres and particles of inorganic oxides or inorganic fibers such as, e.g., ceramic or glass fibers.

Particularly preferably, membranes are used which have a polymer layer of polydimethylsiloxane, polyimide, polyamide-imide, acrylonitrile/glycidyl methacrylate (PANGMA), polyamide or polyether ether ketone as active separation layer and which are made up of polymers having intrinsic microporosity (PIM) such as PIM-1, or wherein the active separation layer is built up over a hydrophobized ceramic membrane. Very particularly preferably, membranes of silicones or polyamide-imide are used. Such membranes are commercially available.

In addition to the abovementioned materials, the membranes can have further materials. In particular, the membranes can have support or carrier materials on which the active separation layer is applied. In such composite membranes, in addition to the actual membrane, a support material is further present. A selection of support materials is described in EP0781166, which is hereby explicitly incorporated by reference.

A selection of commercially available nanofiltration membranes are the MPF and Selro series from Koch Membrane Systems, Inc., various types of Solsep BV, the Starmem™ series from Grace/UOP, the DuraMem™ and PuraMem™ series from Evonik Industries AG, the Nano-Pro series from Bio-Pure Technology, the HITK-T1 from IKTS, and oNF-1, oNF-2 and NC-1 from GMT Membrantechnik GmbH.

According to a further preferred embodiment of the invention, a heat exchanger for heating or cooling the feed or the permeate of the membrane separation stage is arranged in the external liquid circuit, in particular upstream of the membrane separation stage. The heat exchanger generally serves for introducing heat energy into the system in the case of endothermic reactions. In the case of exothermic reactions, the heat of reaction is removed via the heat exchanger.

Depending on the reaction temperature, placing the membrane separation upstream or downstream of the heat exchanger in the outer liquid circuit can be advantageous for the membrane separation. Higher temperatures generally lead to higher permeabilities, but, depending on the membrane material, can lead to a reduction of the membrane retention.

In a further preferred embodiment of the invention, a tubular reaction space extends in the jet loop reactor, into which tubular reaction space a jet nozzle for injecting the liquid into the reaction space and also a suction tube for extracting the gas by suction both open out, and on which is provided a baffle plate-shielded takeoff for the external liquid circuit.

The jet nozzle can be directed upwardly or downwardly in the vertically extending reactor. The conjoint opening of jet nozzle and suction tube effects an intense mixing of the liquid and gaseous reaction components (water pump effect). The gas can be taken in via the suction tube from the outside, or from a region within the reaction space in which a gas bell extends. The takeoff can be arranged at the top or bottom on the reactor. The shielding of the takeoff by the baffle plate decreases the introduction of gas bubbles from the internal liquid circuit into the external liquid circuit.

For improvement of flow dynamics, at least one guide tube which extends concentrically through the reaction space can be provided. The liquid and gaseous phase mixing is intensified thereby. Also, a plurality of guide tubes can be arranged successively so as to align. The reaction mixture then flows through the guide tube in the main direction of flow, is reversed at the end of the guide tube and flows back outside the guide tube. The guide tube is a structural separation of the two directions of flow of the internal loop.

When jet loop reactor and membrane separation stage are arranged in a shared external liquid circuit this means that the throughput through reactor and membrane must be identical. For reasons of apparatus, the throughput rate of reactor and membrane can be different, however. In order then, nevertheless, to implement a liquid circuit or ideal membrane overflow, it is possible to equip the apparatus with the low throughput rate using a bypass conduit which permits a partial bypass of the hydraulic obstacle. Accordingly, the device has at least one bypass conduit which is arranged in the external liquid circuit in parallel to the jet loop reactor or to the membrane separation stage.

In a further preferred embodiment of the device, it has not only one, but a multiplicity of jet loop reactors that are connectable in parallel and have a shared external liquid circuit, wherein the membrane separation stage is arranged within the shared external liquid circuit. A plurality of jet loop reactors that are specifically dimensioned to be smaller permit flexible adaptation of the throughput rate of the device to the demand state by connecting and disconnecting individual reactors. This permits economic utilization of the device in the case of changing demand.

The membrane separation stage can accordingly also be constructed in a parallel manner: By connecting and disconnecting individual membrane modules connected in parallel, the entire membrane area of the membrane separation stage can be flexibly adapted to the plant capacity. A preferred development of the invention is therefore characterized by a membrane separation stage which comprises a multiplicity of membranes that are connectable in parallel in such a manner that the entire active membrane surface area of the membrane separation stage is adjustable by connecting and disconnecting the membranes.

The device according to the invention is outstandingly suitable for the homogeneous-catalytic reaction of a liquid with a gas and optionally a further fluid, in which the target product of the reaction is discharged from the liquid circuit with the permeate of the membrane separation stage.

The invention thus also relates to a process for the homogeneous-catalytic reaction of a liquid with a gas and optionally a further fluid, wherein the reaction is carried out in a device according to the invention, and wherein the target product of the reaction is discharged from the liquid circuit together with the permeate of the membrane separation stage.

In particular when a membrane separation stage is used which has a permeate-side free volume of at least 0.3 dm$^3$ per m$^2$ membrane area, it is possible to process a liquid circuit having a gaseous fraction. This is possible up to a gas fraction of about 30% by volume. In the case of gas fractions of such a level, however, the permeate-side free volume must be chosen to be markedly greater than 0.3 dm$^3$. A preferred development of the process according to the invention is thus that the external liquid circuit upstream of the membrane separation stage is a mixture which comprises a liquid phase and a gaseous phase dispersely distributed therein, wherein the volume fraction of the gaseous phase is between zero and thirty percent.

These reactions can be two-phase (liquid/gaseous) or three-phase (liquid/liquid/gaseous or liquid/gaseous/gaseous). In the liquid circuit, small solids fractions can also be present.

Examples of the reactions which can be carried out are oxidations, epoxidations, hydroformylations, hydroaminations, hydroaminomethylations, hydrocyanations, hydrocarboxyalkylation, aminations, ammonoxidation, oximations, hydrosilylations, ethoxylations, propoxylations, carbonylations, telomerizations, methatheses, Suzuki couplings or hydrogenations.

Particularly preferably, the device is suitable for hydroformylation, that is for reacting compounds having olefinic double bonds with synthesis gas to form aldehydes and/or alcohols.

The use of the described device for carrying out said processes is likewise subject matter of the invention.

The device according to the invention can be used, inter alia, for reacting a liquid with a gas, wherein both the gas and the liquid have at least one reactant.

The reaction products are discharged in the liquid phase together with the permeate.

In the apparatus according to the invention, reactions can be carried out in the pressure range from 0.2 to 40 MPa (absolute) and in the temperature range from 0 to 350° C. The reaction takes place in this case preferably in the presence of a catalyst that is homogeneously dissolved in the liquid phase.

Preferably, in the device according to the invention, reactions are carried out in which the catalyst is fed in together with the liquid feed and is homogeneously dissolved in the liquid product/starting material phase, such as, for example, the production of aldehydes and/or alcohols by hydroformylation of compounds having olefinic double bonds in the presence of cobalt or rhodium carbonyls with or without the addition of phosphorus-containing ligands.

The invention will now be described in more detail with reference to exemplary embodiments. In the drawings:

FIG. 1: shows a device according to the invention having a jet loop reactor

Figure 2:
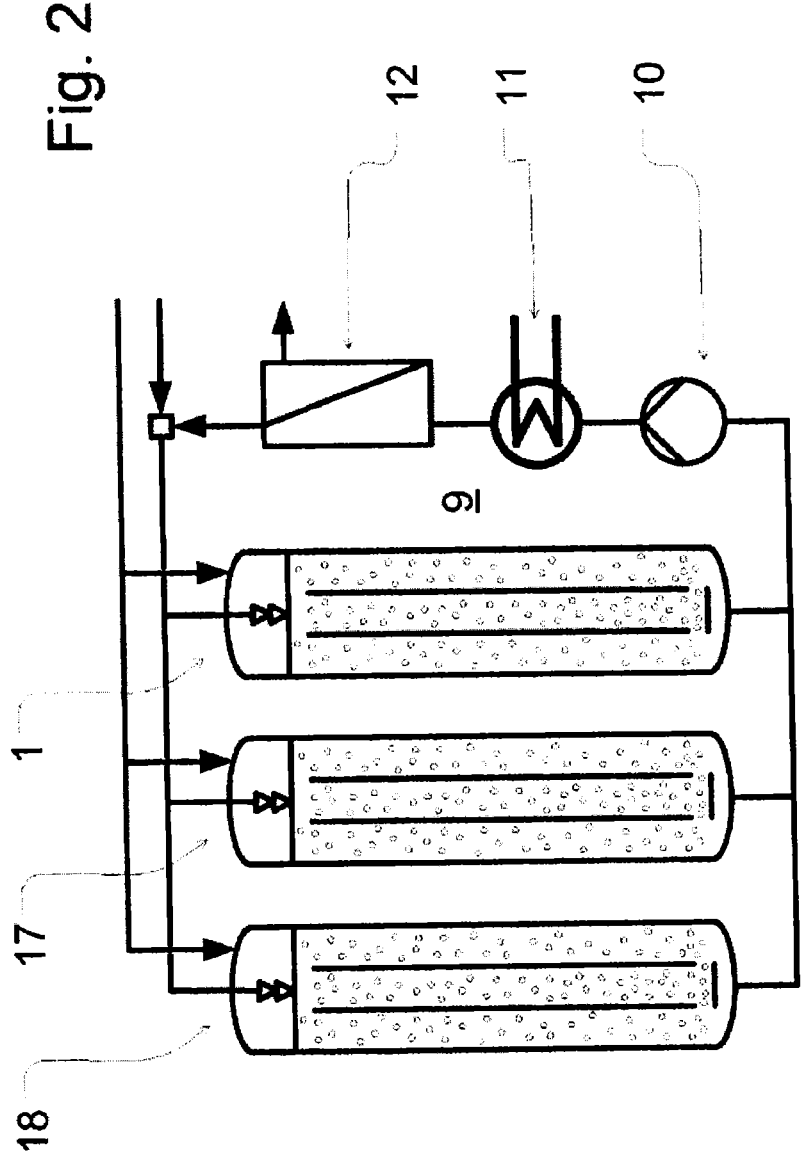
Figure 3:
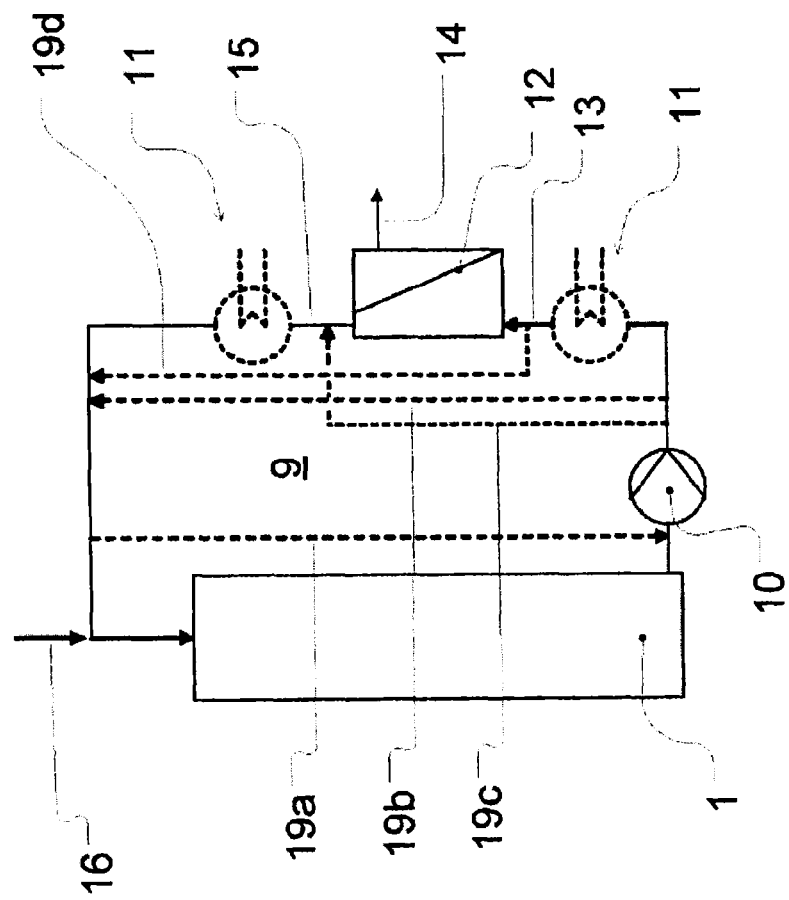
Figure 4:
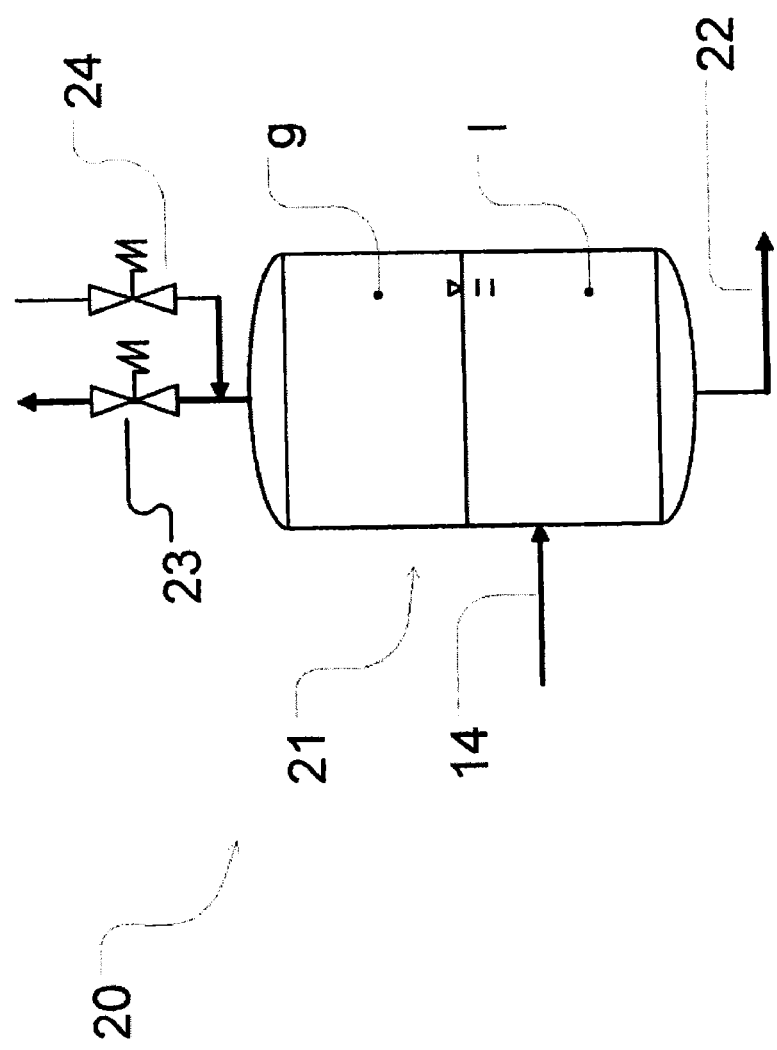
Figure 10:
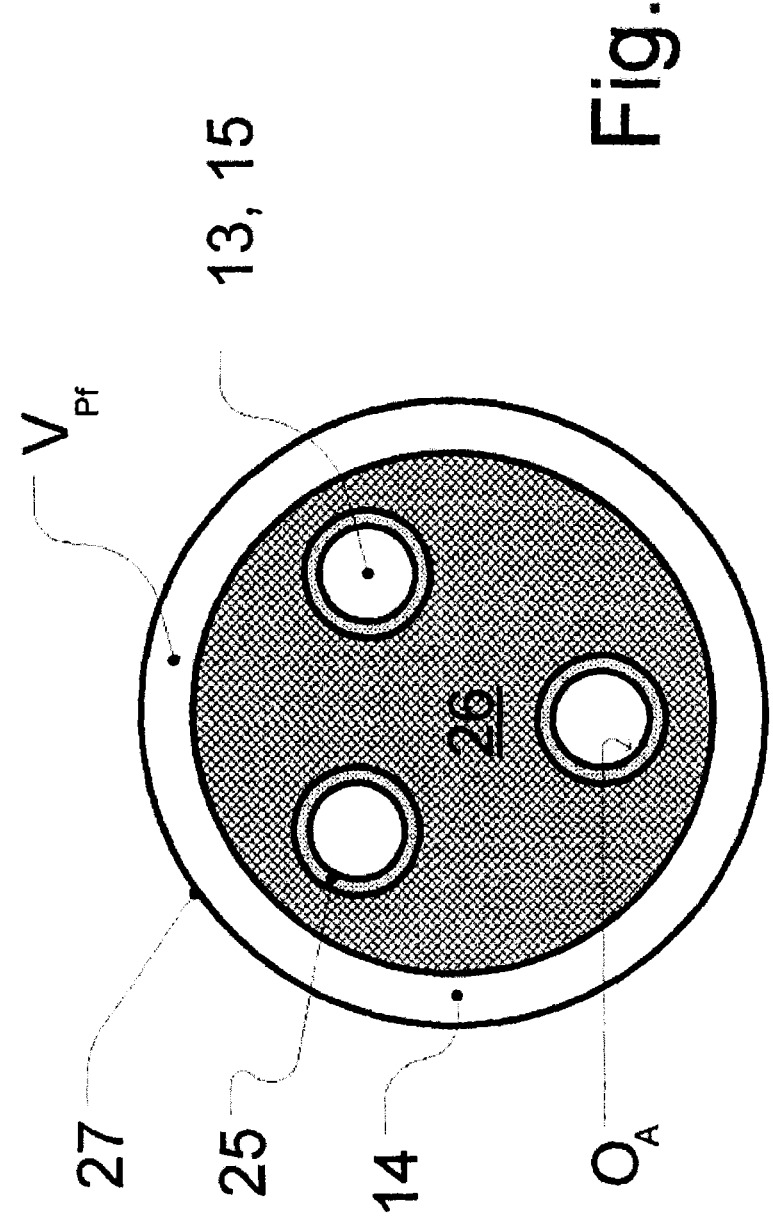

FIG. 2: shows a device according to the invention having a plurality of jet loop reactors FIG. 3: shows a device according to the invention having a plurality of bypass options;

FIG. 4: shows a schematic of a degassing;

FIG. 5: shows a schematic of permeate-side free volume in the case of a membrane having a permeate placeholder;

FIG. 6: shows a schematic of permeate-side free volume in the case of a membrane without permeate placeholder;

FIG. 7: shows a tubular membrane module, schematically in axial view;

FIG. 8: shows a tubular membrane module of FIG. 7 in longitudinal section;

FIG. 9: shows a tubular membrane module comprising a bundle of tubular membranes;

FIG. 10: shows a tubular membrane module comprising a bundle of tubular membranes having a shared support structure.

FIG. 1 shows a first embodiment of the device according to the invention having a jet loop reactor 1. The jet loop reactor 1 comprises a tubular reaction space 2 in the form of a pressure tube which is filled with liquid reaction mixture up to a defined liquid level 3. A gas bell of gaseous reaction participants forms above the liquid level. On account of the dissolution equilibrium, the gaseous reaction participants are in part dissolved in the liquid reaction mixture, and in part gaseous reaction participants are located as gas phase in the liquid (in the drawing shown as gas bubbles). Also dissolved in the reaction liquid is the homogeneous catalyst.

A jet nozzle 4 projects downwards into the liquid reaction mixture, via which jet nozzle liquid reaction participants are injected with high kinetic energy Gaseous reaction participants pass through a gas feed 5 into the reaction space 2. A suction tube is assigned structurally to the steel nozzle 4, which suction tube takes in by suction the gas from the gas-filled part of the reaction space 2 and mixes it with the fluid stream. The orifices of suction tube and jet nozzle are closely adjacent for this purpose and open out together into the reaction space. The gaseous reaction participants are entrained by the high flow velocity of the liquid reaction participants exiting from the jet nozzle 4 (comparable with a water-jet pump).

A guide tube 6 extends concentrically and coaxially to the pressure tube through the reaction space 2. The guide tube 6 serves for creating an internal liquid circuit within the reaction space 2: The injected reaction liquid flows from the jet nozzle 4 down through the guide tube 6 and is reversed by the baffle plate 7 arranged at the other end of the reaction space 2, in such a manner that the stream flows back up outside the guide tube 6. In this manner an internal liquid circuit is formed within the reaction space 2, in which internal liquid circuit the reaction partners are intensely mixed and reacted.

Below the baffle plate 7 a takeoff 8 is provided, through which reaction mixture is continuously taken off from the reaction space 2 and fed into an external liquid circuit 9. The baffle plate 7 shields the takeoff 8 for the internal liquid circuit in such a manner that gas bubbles scarcely pass into the external liquid circuit 9. The external liquid circuit therefore predominantly comprises liquid reactants, dissolved catalyst and dissolved gaseous reactants.

For performance of the invention it is unimportant whether jet nozzle 4 is directed downwards and baffle plate 7 is arranged below the jet nozzle 4. It is also possible to inject upwards from the bottom of the reactor. The takeoff can be arranged in both cases at the top or bottom in the reactor. The baffle plate must correspondingly be arranged in such a manner that it shields the takeoff.

The external liquid circuit 9 is moved by a pump 10. The pump 10 is a peripheral impeller pump which is also able to transport liquid/gaseous mixtures. Insignificant gas bubbles are therefore harmless.

A heat exchanger 11 is arranged downstream of the pump 10, by means of which heat exchanger, depending on the type of reaction, heat can be introduced into or discharged from the external liquid circuit 9. Furthermore, the jet loop reactor 1 can itself be provided with a heat exchanger (which is not shown) which surrounds the reaction space.

A membrane separation stage 12 is arranged downstream of the heat exchanger 11. The membrane separation stage can also be situated upstream of the heat exchanger. As with any membrane, the membrane separation stage 12 has three connections, namely feed 13, permeate 14 and retentate 15. The reaction mixture flowing in via the feed 13 is separated at the membrane into permeate 14 and retentate 15. Since the membrane is less permeable to the dissolved catalyst complex than to the remaining feed components, the catalyst remains this side of the membrane and is enriched in the retentate 15. In relation to the catalyst, the membrane has a better permeability to the products of value, and so the products of value are enriched in the permeate 15 relative to the catalyst. The permeate 14 is conducted further for workup (not shown); the catalyst-rich retentate 15 is returned to the reactor 1 mixed with fresh liquid starting material 16 via the jet nozzle 4.

In order to prevent damage to the membrane and deactivation of the catalyst, uncontrolled degassing of dissolved gaseous reaction participants must be avoided at the membrane 12 and a minimum CO partial pressure in the permeate 14 must be ensured. This is achieved by a separately provided degassing element (see below under FIG. 4) and/or by suitable dimensioning of the free volume of the membrane (see below under FIGS. 5 to 10). In addition, the shielding of the takeoff 8 by means of a baffle plate 7 aids avoiding as far as possible gas bubbles in the feed 13 to the membrane separation stage 12.

FIG. 2 shows a second embodiment of the device according to the invention. It comprises three parallel-connected jet loop reactors 1, 17, 18, each of which is constructed as for the described first jet loop reactor 1. All three jet loop reactors 1, 17, 18 share the joint external liquid circuit 9 in which pump 10, heat exchanger 11 and membrane separation stage 12 are used jointly. The advantage of the parallel arrangement is a better adaptability of the plant to changing demand: At base load, two jet loop reactors 1, 17 should run, at high demand the third 18 can be connected in, and at low demand the second 17 is also disconnected, in such a manner that the plant operates with only one reactor 1. The reactors 1, 17, 18 must correspondingly be provided with suitable disconnecting elements (which are not shown). Owing to the switchable parallel connection, a better plant utilization is possible. Furthermore, each individual (connected) reactor can always be operated in the optimum operating state with respect to flow dynamics. Partial load operation is very largely prevented. By changing the speed of rotation, the pump is adapted to the respective volumetric flow rates. The adaptation of the total active surface area of the membrane separation stage is likewise possible by suitable parallel connection of a plurality of membranes.

FIG. 3 shows various developments of the invention, each of which has a bypass conduit 19a, 19b, 19c, 19d.

As described above, the plant according to this embodiment also comprises a jet loop reactor 1, in the external liquid circuit 9 of which is arranged a pump 10 and a membrane separation stage 12 for removing the product together with the permeate 14. Starting material 16 is injected into the reactor 1. An optional heat exchanger 11 can be arranged in the feed 14 or in the retentate 15 of the membrane separation stage 15. A precondition of the maintenance of the liquid circuit 9 is that the mass throughput through the reactor 1 is the same as through the membrane (starting material 16 and product in the permeate 14 balance out). Since the residence time in the reactor can demand a different mass flow rate, however, than the ideal membrane overflow offers, depending on the process, a bypass conduit 19 is necessary, each of which runs in parallel to the "slower" plant element. Thus, bypass 19a can run in parallel to the slower reactor 1; in the event that the reactor is faster, the bypass 19b must be arranged in parallel to the membrane separation stage 12. If the heat exchanger 11 is the limiting factor, bypass 19c must be provided in the feed for the heat exchanger, or bypass 19d must be provided in the retentate for the heat exchanger. In each case a corresponding substream flows through the bypass round the respective plant element. The other part of course flows further through the element. The bypass is therefore not a complete bridging, but merely opens a hydraulically expedient alternative path.

FIG. 4 shows an optional degassing 20 which can be arranged in the permeate stream 14 of the membrane separation stage in order to prevent uncontrolled degassing at the membrane. The degassing comprises a pressure vessel 21 in which a liquid phase I and a gaseous phase g separate from one another. The product-containing liquid phase I is taken off via a product takeoff 22. The pressure of the gaseous phase is controlled by throttles 23, 24. If the pressure is excessive, gas is taken off via throttle 23. If the pressure in the vessel falls, which can lead to degassing at the membrane, the pressure vessel 21 is charged with gas from the outside via throttle 24. The transmembrane pressure of the membrane separation stage 12 can also be adjusted via the degassing 20.

Since commercially available membrane modules are not able to pass through gas fractions in the liquid stream in the long term without damage, according to the invention it is proposed to dimension the permeate-side free volume with at least 0.3 dm³ per m² of membrane area. The free permeate-side volume is explained with reference to FIGS. 5 to 10.

FIG. 5 shows the schematic structure of a planar membrane separation stage. The membrane comprises an active separation layer 25 and a porous support layer 26 arranged downstream with the permeate. The separation takes place at the active separation layer 25, the support layer 26 mechanically stabilizes the active separation layer 25. The membrane module is either symmetrically constructed (line of symmetry 27) or unsymmetrically constructed. In this case, line 27 denotes the opposite wall of the membrane module. A permeate placeholder 28 (also termed permeate spacer) can be provided with the permeate further downstream, for example a coarsely porous structure or a grating or a mesh.

The feed 13 flows along the active separation layer 25, is depleted in the permeating components thereof, and leaves the membrane as retentate 15. The permeate 14 passes through the active separation layer 26 and leaves the membrane separation stage. The permeate-side volume $V_P$ is understood as the permeate-side volume following perpendicularly to the active membrane surface area $O_A$ (surface area of the active separation layer 25). This extends along the height h up to the line of symmetry or wall 27 of the membrane separation stage. Thus, for planar membrane systems, or else in approximation to flat channel systems as with the spiral wound element, the following applies:

$$V_P = O_A \times h.$$

The free permeate-side volume $V_{Pf}$ is the fraction of the permeate-side volume $V_P$ which is not filled by the material of the active separation layer 25, the support layer 26 and the permeate placeholder 28. In operation, this space is occupied by permeate. It may accordingly be measured volumetrically by charging a test liquid (termed "volumetric measurement").

The free permeate-side volume $V_{Pf}$ is adjusted by dimensioning the permeate placeholder 28 since the porosity of the active separation layer 25 is determined by the separation task and that of the support layer 26 by the mechanical load.

The permeate-side free volume $V_{Pf}$ must be adjusted according to the invention in such a manner that the following applies:

$$V_{Pf}[dm^3] \geq 0.3 \times O_A [M^2]$$

Dispensing with a permeate placeholder shown in FIG. 6 increases the permeate-side free volume $V_{Pf}$, provided that the remaining dimensions of the membrane are retained.

In FIGS. 5 and 6, flow passed through the membrane from the outside to the inside. There are also membrane modules in which flow passes through the membranes from the inside to the outside. Thus, FIG. 7 outlines a tubular membrane module in which feed 13 and permeate 15 flow axially through a cylindrical inner channel 29 which is surrounded by the active separation layer 25. The support layer 26 follows this radially towards the exterior. The permeate 14 flows off from the membrane module through an annular outer channel 30 which surrounds the support layer 26 and is itself sealed off from the outside by the wall 27 of the membrane module. The permeate-side volume $V_P$ is thus calculated from the product of the active membrane surface area $O_A$ and the height h.

FIG. 8 shows a longitudinal section through the tubular membrane module of FIG. 7.

FIG. 9 shows a variant of a tubular membrane module in which a multiplicity of cylindrical inner channels 29 are bundled within the wall 27 of a tube. Each inner channel 29 is surrounded by a cylindrical active separation layer 25 and a cylindrical support layer 26. In calculation of the permeate-side volume, therefore, the packing density of the channels 29 must be taken into account. For the active membrane surface area $O_A$, the total of the shell surfaces of the inner channels 29 formed by the active separation layer 25 must be formulated. A switchable parallel connection of the membranes may be effected by optional disconnection of the individual inner channels 29 by suitable disconnecting elements. Flexible adaptation of the entire active surface area of the membrane separation stage to the demand situation is thereby possible.

FIG. 10 shows a further variant of a tubular membrane module in which a multiplicity of inner channels 29 are bundled within the wall 27 of a tube, wherein the inner channels 29, however, share a common support structure 26.

Using the combination according to the invention of a jet loop reactor with a membrane separation stage, gas/liquid reactions, in particular hydroformylations, may be carried out more economically than with reactors traditionally used in the industry.

EXAMPLES

1. Membrane Pretesting

Studies on permeate flux determination and retention measurement were carried out for preselecting suitable membranes. A 1-pentene hydroformylation reaction mixture was charged into a 5 l reservoir. The composition of the reaction mixture is given in table X. As catalyst ligand system, 10 mg/kg of rhodium and 1170 mg/kg of Alkanox P-24 (CAS No. 26741-53-7) are present.

TABLE X

| 1-Pentene [% by wt.] | 2-Methylpentanal [% by wt.] | Hexanal [% by wt.] | Remainder [% by wt.] |
|---|---|---|---|
| 6.996 | 47.960 | 43.932 | 1.112 |
| 6.894 | 47.774 | 43.585 | 1.747 |

The reaction mixture was conducted over the tested membranes at 25° C., a transmembrane pressure difference of 4 bar and an overflow of 200 l/h.

TiO₂ monochannel membranes of the Innopor® nano type having a median pore size of 0.9 nm, a separation limit of 450 Da and an open porosity of 0.3 to 0.4 from Innopor GmbH were tested. At a channel length of 500 mm and an internal diameter of 7 mm, an active membrane surface area of approximately 100 cm² results.

The results of the permeability measurements are shown in table Y. Permeabilities in two different orders of magnitude result. Four of eight tested membranes are in the range from 0.8 to 2.9 kg/(m² h bar). The other four membranes are in the range from 18 to 37 kg/(m² h bar).

TABLE Y

| Membrane Number | Permeability [kg/(m²h bar)] |
|---|---|
| 1 | 0.8 |
| 2 | 19 |
| 3 | 37 |
| 4 | 18 |
| 5 | 29 |
| 6 | 1.6 |
| 7 | 1.5 |
| 8 | 2.9 |

In a further test for determining retention, isopropanol was charged into the reservoir. Rose bengal (CAS No. 11121-48-

5) having a molar mass of 974 g/mol was used as a marker for determining retention. Retentions from 93 to 97% were found for the membranes having permeabilities in the range from 0.8 to 2.9 kg/(m²h bar). For the membranes having permeabilities in the range from 18 to 37 kg/(m²h bar), retentions from 55 to 61% were found. Since the membranes, according to the manufacturer's instructions, should have a separation limit of 450 g/mol, the membranes having high permeability and low retention for Rose bengal were rejected as defective.

2. Example According to the Invention (0.9 nm)

In an experimental plant as shown in FIG. 1 having a jet loop reactor (1), hydroformylation reactions of 1-pentene (16) with synthesis gas (5) to give the corresponding aldehyde isomers were carried out. In the liquid circuit (9) driven by a peripheral impeller pump (10), the catalyst-ligand system was separated off and returned by means of a membrane separation stage (12) for continuous reuse of the catalyst-ligand system in the hydroformylation reaction in the jet loop reactor (1).

For the reaction, 1-pentene (16) was fed to the reactor in the absence of oxygen continuously via the permeate of the membrane separation stage in accordance with the reaction product removal. The catalyst precursor was rhodium acetylacetonatodicarbonyl (CAS No. 14847-82-9). The ligand used was Alkanox P-24 (CAS No. 26741-53-7). The rhodium concentration and the ligand concentration in the loop reactor was held constant at 10 mg/kg and 1170 mg/kg, respectively, by continuous replenishment. The reaction was carried out under 50 bar synthesis gas pressure (CO/$H_2$, mass ratio 1:1) at 110° C.

The reaction product was continuously conducted through a membrane separation stage (12) constructed as a one-stage nanofiltration membrane. The transmembrane pressure required is built up by the reactor pressure and a controlled permeate-side (14) pressure. The desired overflow of 500 kg/h over the high-pressure side of the membrane is adjusted via the peripheral impeller pump.

Membrane number 1 of example 1 was installed in the membrane module of the membrane separation stage (12).

At a channel length of 500 mm and an internal diameter of 7 mm, an active membrane surface area of approximately 100 cm² results. The permeate-side free volume based on the membrane area is greater than 0.5 dm³/m². The overflow over the membrane was 4.4 m/s. The temperature in the membrane separation step was 102° C. A synthesis gas pressure (CO/$H_2$, mass ratio 1:1) of 10 bar was held on the permeate side using a device according to FIG. 4 for stabilizing the catalyst-ligand complex, as a result of which a transmembrane pressure of 40 bar was set at a retentate-side pressure of 50 bar. The low pressure of the permeate side leads to outgassing of synthesis gas. The two-phase permeate stream (14) is fed to a degassing appliance (FIG. 4).

Permeate (14) which consists predominantly of reaction product was withdrawn from the system via the membrane in the membrane separation stage. The catalyst and the ligand Alkanox were very largely retained by the membrane and accumulate in the retentate (15). The retentate (15) was continuously fed back to the jet loop reactor (1).

The process chain was evaluated on the basis of measurement and analytical data which were obtained by gas-chromatographic analysis, HPLC analysis, atomic absorption spectroscopy and optical emission spectrometry with inductively coupled high-frequency plasma. The reaction was studied with respect to the conversion rate of 1-pentene and also the yield and selectivity of aldehyde. The membrane separation stage (12) was studied with respect to permeate flux and retention of rhodium and ligand. The conversion rate of 1-pentene was 95%, and the aldehyde selectivity was 98%.

The $TiO_2$ monochannel membrane of the Innopor® nano type showed a membrane retention rate between 88 and 92% with respect to the rhodium at specific permeate flux output between 53 and 57 kg/m² h. The retention of the ligand was 83%.

The example shows that the homogeneous catalyst could be quantitatively retained and recirculated to the loop reactor using the selected membrane separation stage in the liquid circuit of the loop reactor. The specific free permeate volume of the membrane separation stage which was sufficiently high made possible a high retention of the catalyst system and enabled an unrestrictedly good permeate flux despite the permeate-side degassing. In addition, the catalyst was retained in active form with a nanofiltration under the selected conditions.

3. Example According to the Invention (3 nm)

1-Pentene (16) hydroformylation reactions with synthesis gas (5) to give the corresponding aldehyde isomers were carried out in an experimental plant as shown in FIG. 1 having a jet loop reactor (1). The catalyst-ligand system was separated off and recirculated in the liquid circuit (9) driven by a peripheral impeller pump (10) by means of a membrane separation stage (12) for continuous reuse of the catalyst-ligand system in the hydroformylation reaction in the jet loop reactor (1).

For the reaction, 1-pentene (16) was fed continuously to the reactor in the absence of oxygen via the permeate of the membrane separation stage in accordance with the reaction product removal. The catalyst precursor was rhodium acetylacetonatodicarbonyl (CAS No. 14847-82-9). The ligand used was Alkanox P-24 (CAS No. 26741-53-7). The rhodium concentration and the ligand concentration in the loop reactor were held constant at 10 mg/kg and 1170 mg/kg, respectively, by continuous replenishment. The reaction was carried out at 50 bar synthesis gas pressure (CO/$H_2$, mass ratio 1:1) at 110° C.

The reaction product was conducted continuously through a membrane separation stage (12) constructed as a one-stage nanofiltration membrane. The transmembrane pressure required is built up by the reactor pressure and a controlled permeate-side (14) pressure. The desired overflow of 500 kg/h over the high-pressure side of the membrane is established via the peripheral impeller pump.

A prototype of a membrane hydrophobized by silanization was built into the membrane module of the membrane separation stage (12) as a monochannel tube by the Fraunhofer-Institut für Keramische Technologien und Systeme IKTS [Fraunhofer Institute for Ceramic Technologies and Systems]. The carrier consisted of $Al_2O_3$ having a median pore size of 3 μm and a hydrophobized membrane layer based on a $ZrO_2$ layer having a median pore diameter of 3 nm.

At a channel length of 500 mm and an internal diameter of 7 mm, an active membrane area of approximately 100 cm² results. The permeate-side free volume based on the membrane area is greater than 0.5 dm³/m². The overflow across the membrane was 4.4 m/s. The temperature in the membrane separation step was 101° C. A synthesis gas pressure (CO/$H_2$, mass ratio 1:1) of 10 bar was held for stabilizing the catalyst-ligand complex on the permeate side using a device according to FIG. 4, as a result of which a transmembrane pressure of 40 bar was established at a retentate-side pressure of 50 bar. The low pressure of the permeate side leads to outgassing of synthesis gas. The two-phase permeate stream (14) is fed to a degassing appliance (FIG. 4).

Permeate (14) which predominantly comprises reaction product was taken off from the system in the membrane separation stage. The catalyst and the ligand Alkanox were very largely retained by the membrane and accumulate in the retentate (15). The retentate (15) was continuously returned to the jet loop reactor (1).

The process chain was evaluated on the basis of measurement and analytical data which were obtained by gas-chromatographic analysis, HPLC analysis, atomic absorption spectroscopy and optical emission spectrometry with inductively coupled high-frequency plasma. The reaction was studied with respect to the conversion rate of 1-pentene and the yield and selectivity of aldehyde. The membrane separation stage (12) was studied with respect to permeate flux and retention of rhodium and ligand. The conversion rate of 1-pentene was 94%, and the aldehyde selectivity was 98%.

The prototype membrane showed a membrane retention with respect to rhodium between 73 and 74% at specific permeate flux outputs between 96 and 98 kg/m²h. The retention of the ligand was 64%.

Example 2 also shows that the homogeneous catalyst was able to be retained quantitatively and returned to the loop reactor using the selected membrane separation stage in the liquid circuit of the loop reactor. The specific free permeate volume of the membrane separation stage that is sufficiently high permitted a high retention of the catalyst system and an unrestrictedly good permeate flux despite the permeate-side degassing. In addition, the catalyst was retained in active form using a nanofiltration under the selected conditions.

4. Example

In this example the effect of gas loading under conditions as constant as possible in the membrane separation stage with respect to retentate pressure, permeate pressure and temperature is to be demonstrated. For this purpose the experimental setup of example 2 and example 3 according to FIG. 1 was extended by a pressurizing pump in the liquid circuit (9) downstream of the loop reactor (1) and upstream of the bypass conduit (19a, FIG. 3). This is necessary, since the feed pressure of the membrane should sometimes be above the synthesis gas pressure in the reactor in the experiments. The peripheral impeller pump (10) in addition generates the overflow of the membrane separation stage.

1-Pentene (16) hydroformylation product according to the composition of table X of example 1 was charged in the jet loop reactor (1). The catalyst-ligand system was separated off and returned to the jet loop reactor (1) by means of a membrane separation stage (12) for the catalyst-ligand system in the liquid circuit (9) driven by the peripheral impeller pump (10).

The synthesis gas pressure ($CO/H_2$, mass ratio 1:1) was varied in the jet loop reactor (1) from 10, 20, 30, 40, 50 bar.

The reaction product charged with synthesis gas was continuously conducted via a membrane separation stage (12) constructed as a one-stage nanofiltration membrane. The transmembrane pressure required is held at 40 bar by the additional pump in the liquid circuit. The desired overflow of 500 kg/h over the high-pressure side of the membrane is established via the peripheral impeller pump.

Membrane number 1 of example 1 was installed in the membrane module of the membrane separation stage (12). At a channel length of 500 mm and an internal diameter of 7 mm, an active membrane area of approximately 100 cm² results. The permeate-side free volume based on the membrane area is greater than 0.5 dm³/m². The overflow over the membrane was 4.4 m/s. The temperature in the membrane separation step was 60° C. A synthesis gas pressure ($CO/H_2$, mass ratio 1:1) of 10 bar was held on the permeate side using a device according to FIG. 4 to stabilize the catalyst-ligand complex, as a result of which a transmembrane pressure of 40 bar was set at a retentate-side pressure of 50 bar. The low pressure of the permeate side leads to a corresponding amount of outgassing synthesis gas on the permeate side, depending on the level of the synthesis gas pressure in the loop reactor. The two-phase permeate stream (14) is fed to a degassing appliance (FIG. 4).

Permeate (14) which predominantly comprises reaction product was taken off from the system via the membrane in the membrane separation stage. The rhodium complex and the free ligand were very largely retained by the membrane and accumulate in the retentate (15). The retentate (15) was continuously returned to the jet loop reactor (1).

The process chain was evaluated on the basis of measurement and analytical data which were obtained by gas-chromatographic analysis, HPLC analysis, atomic absorption spectroscopy and optical emission spectrometry with inductively coupled high-frequency plasma. The membrane separation stage (12) was studied with respect to permeate flux and retention of rhodium and ligand. The results of the example are summarized in table Z1:

TABLE Z1

| Synthesis gas [bar] | TMP [bar] | Temperature [° C.] | Permeate flux [kg/(m²h)] | Rh retention [%] |
|---|---|---|---|---|
| 10 | 40 | 60 | 28.2 | 91.1 |
| 20 | 40 | 60 | 30.1 | 89.8 |
| 30 | 40 | 60 | 29.4 | 90.5 |
| 40 | 40 | 60 | 28.4 | 91.3 |
| 50 | 40 | 60 | 29.7 | 90.0 |

This example shows that the synthesis gas pressure in the reactor and thus the amount of dissolved synthesis gas has no effect on the permeate flux at a permeate-side free volume of greater than 0.5 dm³/m² based on the membrane area.

5. Counterexample in the Membrane Coil

In this example, the effect of gas loading under conditions as constant as possible in the membrane separation stage with respect to retentate pressure, permeate pressure and temperature is to be demonstrated. For this purpose, the experimental setup of example 2 and example 3 according to FIG. 1 was extended by a pressurizing pump in the liquid circuit (9) downstream of the loop reactor (1) and upstream of the bypass conduit (19a, FIG. 3). This is necessary, since in the experiments the feed pressure of the membrane should sometimes be above the synthesis gas pressure in the reactor. The peripheral impeller pump (10) continues to generate the overflow of the membrane separation stage.

1-Pentene (16) hydroformylation product according to the composition of table X of example 1 was charged in the jet loop reactor (1). In the liquid circuit (9) driven by the peripheral impeller pump (10), the catalyst-ligand system was separated and returned to the jet loop reactor (1) by means of a membrane separation stage (12) for the catalyst-ligand system. The synthesis gas pressure ($CO/H_2$, mass ratio 1:1) was varied in the jet loop reactor (1) from 10, 20, 30, 40, 50 bar.

The reaction product charged with synthesis gas was conducted continuously via a membrane separation stage (12) constructed as a one-stage nanofiltration membrane. The transmembrane pressure required is kept at 40 bar by the additional pump in the liquid circuit. The desired overflow of 250 kg/h over the high-pressure side of the membrane is set via the peripheral impeller pump.

A 1.8" times 12" membrane spiral coil having a membrane of the ONF2 type from GMT Membrantechnik GmbH was installed in the membrane module of the membrane separation stage (12). The feed spacer had a height of 31 mm and the permeate spacer had a height of 10 mm. This gives an active membrane area of approximately 0.1 m². The permeate-side free volume based on the membrane area is less than 0.1 dm³/m². The temperature in the membrane separation step was 60° C. A synthesis gas pressure (CO/H₂, mass ratio 1:1) of 10 bar was held on the permeate side using a device according to FIG. 4 for stabilizing the rhodium-ligand complex, as a result of which, at a retentate-side pressure of 50 bar, a transmembrane pressure of 40 bar was established. The low pressure of the permeate side leads to a corresponding amount of outgassing synthesis gas on the permeate side, depending on the height of the synthesis gas pressure in the loop reactor. The two-phase permeate stream (14) is conducted to a degassing appliance (FIG. 4).

In the membrane separation stage, permeate (14) that predominantly comprises reaction product was taken off from the system via the membrane. The rhodium complex and the free ligand were very largely retained by the membrane and accumulate in the retentate (15). The retentate (15) was continuously returned to the jet loop reactor (1).

The process chain was evaluated on the basis of measurement and analytical data which were obtained by gas-chromatographic analysis, HPLC analysis, atomic absorption spectroscopy and optical emission spectrometry with inductively coupled high-frequency plasma. The membrane separation stage (12) was studied with respect to permeate flux and retention for rhodium and ligand. The results of the example are summarized in table Z2:

TABLE Z2

| Synthesis gas [bar] | TMP [bar] | Temperature [° C.] | Permeate flux [kg/(m²h)] | Rh retention [%] |
|---|---|---|---|---|
| 10 | 40 | 60 | 114 | 96.4 |
| 20 | 40 | 60 | 114 | 94.8 |
| 30 | 40 | 60 | 113 | 96.3 |
| 40 | 40 | 60 | 101 | 93.3 |
| 50 | 40 | 60 | 79 | 94.0 |

This example shows that the synthesis gas pressure in the reactor and thus the amount of dissolved synthesis gas has an effect on the permeate flux. The more synthesis gas can outgas on the permeate side of the membrane, the lower is the permeate flux of the membrane. In the example, the permeate flux at a synthesis gas pressure typical of the reaction of 50 bar is 31% lower than at a synthesis gas pressure of 10 to 20 bar in the reactor. The cause of this is the insufficient permeate-side volume of less than 0.1 dm³/m².

6. Example: Long-Term Testing

The membrane of example 5 was studied in a long-term experiment. The reaction procedure corresponds to examples 2 and 3. The reaction was carried out under 50 bar synthesis gas pressure (CO/H₂, mass ratio 1:1) at 110° C.

The reaction product was first conducted through a heat exchanger (11, FIG. 3) and then through a membrane separation stage (12) constructed as a one-stage nanofiltration membrane. The temperature in the membrane separation step was 60° C. The required transmembrane pressure is built up by the reactor pressure and a controlled permeate-side (14) pressure. The desired overflow of 250 kg/h over the high-pressure side of the membrane is established via the peripheral impeller pump. A synthesis gas pressure (CO/H₂, mass ratio 1:1) of 10 bar was held on the permeate side for stabilizing the rhodium-ligand complex using a device according to FIG. 4, as a result of which a transmembrane pressure of 40 bar was established at a retentate-side pressure of 50 bar. The low pressure of the permeate side leads to outgassing of synthesis gas. The two-phase permeate stream (14) is conducted to a degassing appliance (FIG. 4). A second heat exchanger (11, FIG. 3) in the liquid circuit heats the circuit back to reaction temperature.

Permeate (14) that predominantly comprises reaction product was withdrawn from the system via the membrane in the membrane separation stage. The rhodium complex and the free ligand were very largely retained by the membrane and accumulated in the retentate (15). The retentate (15) was continuously returned to the jet loop reactor (1).

The process chain was evaluated on the basis of measurement and analytical data which were obtained by gas-chromatographic analysis, HPLC analysis, atomic absorption spectroscopy and optical emission spectrometry with inductively coupled high-frequency plasma. The reaction was studied with respect to the conversion rate of 1-pentene and also the yield and selectivity of aldehyde. The membrane separation stage (12) was studied with respect to permeate flux and retention of rhodium and ligand. The conversion rate of 1-pentene was 93% and the aldehyde selectivity was 98%.

The ONF2 membrane coil exhibited at specific permeate flux outputs between 73 and 77 kg/m²h. The rhodium retention decreased only insignificantly from 93 to 94% in the course of 9 weeks to 90%. In the 10$^{th}$ week, however, a retention of only 34% was measured. Such membrane damage does not occur in the case of a single-phase flow in the permeate space of such a membrane coil.

LIST OF REFERENCE SIGNS

1 Jet loop reactor
2 Reaction space
3 Liquid level
4 Jet nozzle
5 Gas feed
6 Guide tube
7 Baffle plate
8 Takeoff
9 External liquid circuit
10 Pump
11 Heat exchanger
12 Membrane separation stage
13 Feed
14 Permeate
15 Retentate
16 Starting material
17 Second jet loop reactor
18 Third jet loop reactor
19 Bypass conduit
20 Degassing
21 Pressure vessel
22 Product takeoff
23 Throttle gas takeoff
24 Throttle gas addition
g Gaseous phase in the pressure vessel
l Liquid phase in the pressure vessel
25 Active separation layer
26 Support layer/support structure
27 Line of symmetry/wall
28 Permeate placeholder
$V_P$ Permeate-side volume
$V_{Pf}$ Permeate-side free volume
$O_A$ Active membrane surface area
h Height
29 Inner channel
30 Outer channel

The invention claimed is:

1. A device, comprising:
   a reactor having a pump-driven external liquid circuit; and
   a membrane separation stage configured to retain a homogeneous catalyst,
   wherein
   the reactor is a jet loop reactor,
   the pump and membrane separation stage are configured in the same external liquid circuit, and
   a permeate-side free volume is in the membrane separation stage, wherein a free volume is at least 0.3 dm$^3$ per m$^2$ of a membrane surface.

2. The device of claim 1,
   wherein
   the pump is equipped structurally long-term pumping of fluids which comprise liquid and gaseous phases.

3. The device of claim 2,
   wherein
   the pump is a peripheral impeller pump.

4. The device of claim 1, wherein a permeate-side gas discharge is configured downstream of the membrane separation stage.

5. The device of claim 1,
   wherein
   a heat exchanger adapted for heating or cooling a feed or a permeate of the membrane separation stage is arranged in the external liquid circuit.

6. The device of claim 1,
   wherein
   a tubular reaction space extends in the jet loop reactor, into which a jet nozzle adapted for injecting liquid into the reaction space and a suction tube adapted for extracting gas by suction both open out, and on which is a baffle plate-shielded takeoff adapted for the external liquid circuit.

7. The device of claim 1, wherein a bypass conduit which is arranged in the external liquid circuit is parallel to the jet loop reactor or to the membrane separation stage.

8. The device of claim 1,
   comprising
   a multiplicity of jet loop reactors that are connectable in parallel and have a shared external liquid circuit, wherein the membrane separation stage is arranged within the shared external liquid circuit.

9. The device of claim 8,
   wherein
   the membrane separation stage comprises a multiplicity of membranes that are connectable in parallel in such a manner that an entire active membrane surface area of the membrane separation stage is adjustable by connecting and disconnecting the membranes.

10. The device of claim 1, wherein the device is suitable for carrying out a homogeneous-catalytic reaction.

11. The device of claim 1, wherein a heat exchanger adapted for heating or cooling a teed or a permeate of the membrane separation stage is arranged in the external liquid circuit, upstream of the membrane separation stage.

12. The device of claim 1, wherein the free volume is at least 0.5 dm$^3$ per m$^2$ of a membrane surface.

13. The device of claim 1, wherein the membrane separation stage comprises at least one membrane having a molecular weight cutoff in the range of 150 g/mol to less than 1000 g/mol.

14. The device of claim 13, wherein the free volume is at least 0.5 dm$^3$ per m$^2$ of a membrane surface.

* * * * *